United States Patent [19]

Peterson et al.

[11] 4,086,280

[45] Apr. 25, 1978

[54] PROCESS FOR THE PREPARATION OF CYCLOPROPYLCARINYL ALCOHOLS

[75] Inventors: Donald John Peterson, Cincinnati; Medford Dwight Robbins, Fairfield, both of Ohio

[73] Assignee: The Procter & Gamble Company, Cincinnati, Ohio

[21] Appl. No.: 699,404

[22] Filed: Jun. 24, 1976

Related U.S. Application Data

[60] Division of Ser. No. 586,456, Jun. 12, 1975, abandoned, which is a division of Ser. No. 390,156, Aug. 23, 1973, Pat. No. 3,959,324, which is a continuation-in-part of Ser. No. 247,641, Apr. 26, 1972, abandoned.

[51] Int. Cl.$^2$ ............................................. C07C 29/00
[52] U.S. Cl. ............................. 260/617 R; 260/429.7; 260/618 R
[58] Field of Search ............. 260/617 R, 618 R, 429.7

[56] References Cited

U.S. PATENT DOCUMENTS

| 3,462,453 | 8/1969 | Popoff et al. | 260/617 R |
| 3,636,161 | 1/1972 | Robinson | 260/617 R |

Primary Examiner—Norman Morgenstern
Attorney, Agent, or Firm—Rose Ann Dabek; Julius P. Filcik; Richard C. Witte

[57] ABSTRACT

Pesticidal and anti-inflammatory cyclopropyl compounds, cyclopropyl intermediates for the preparation of pesticidal compounds, especially chrysanthemic acid-like intermediates, and a process for preparing same.

5 Claims, No Drawings

PROCESS FOR THE PREPARATION OF CYCLOPROPYLCARINYL ALCOHOLS

CROSS-REFERENCE TO RELATED APPLICATION

This is a division, of pending prior application Ser. No. 586,456, filed on June 12, 1975, now abandoned which is a divisional of Ser. No. 390,156, filed on August 23, 1973, now U.S. Pat. No. 3,959,324, issued May 25, 1976, which is a continuation-in-part of Ser. No. 247,641, filed Apr. 26, 1972, now abandoned.

BACKGROUND OF THE INVENTION

This invention relates to novel cyclopropyl compounds having biological activity, especially pesticidal and anti-inflammatory activity, and to a method of controlling weeds, insects, bacteria, fungi and other plant and animal pests using certain of these compounds.

A variety of compounds are currently used for the control of insect and plant pests. Included among such pesticidal compounds are chlorinated hydrocarbons, arsenic compounds, mercury compounds and the like. While effective for their intended use, the safety of such materials is currently under question largely because of their poor biodegradability and high mammalian toxicity. Current trends in the chemical control of insect and plant pests call for inherently safer materials which degrade very rapidly to non-toxic substances once their purpose is accomplished. Accordingly, there is great demand for alternative broad spectrum pesticides which are suitable for the high volume usage entailed in agricultural applications.

Of the several types of biodegradable insecticides currently available, those compounds containing a cyclopropyl moiety, e.g., the derivatives of chrysanthemic acid, are of high potential utility inasmuch as these compounds have a relatively low initial mammalian toxicity and biodegrade under field conditions to non-toxic products. However, it has long been recognized that the preparation of compounds containing the cyclopropyl moiety is difficult inasmuch as this 3-membered ring is quite strained and is not readily established by ordinary chemical means. To date, compounds containing the cyclopropyl or cyclopropylcarbinyl group have had to be prepared by such methods as the zinc dust condensation of 1,3-dihalides, a method which yields only small amounts of the desired cyclopropyl derivatives because of intermolecular coupling reactions. The addition of >C: fragments to olefins has also been employed, but requires expensive reactants. Accordingly, improved methods for preparing compounds containing the cyclopropyl moiety would be highly desirable, inasmuch as an economical route to such compounds would provide the basic intermediates for the preparation of a variety of biologically active cyclopropyl derivatives.

Another type of cyclopropyl compounds of interest are the p-(α-cyclopropyl)-tolyl acetic acids which have known anti-inflammatory properties but are difficult to prepare. Such compounds are described in the *Journal of Medical Chemistry*, Vol. 16, No. 5 at 487 (1973).

A variety of methods for preparing compounds containing the cyclopropyl moiety are known in the art. For example, Kuivila and Scrapa, *J. Am. Chem. Soc.* 92:23; 6990 (1970) teach the formation of cyclopropyl groups by an intramolecular electrophilic displacement caused by an internal carbonium ions. Davis, et al., *J. Organometal Chem.*, 25 (1970) C13–C16 teach the reaction of certain organotin alcohols with certain chlorinating agents with cleavage of the organotin compound and elimination of cyclopropane. Sommer, et al., *J. Am. Chem. Soc.*, 71, 2056 (1949) teach the reaction of certain γ-haloalkyl organosilicon compounds with aluminum chloride to yield cyclopropane. Kuivila, et al., *J. Am. Chem. Soc.*, 93, 6990 (1970) disclose the formation of cyclopropyl groups by α,ω eliminations in a number of compounds including 3-toxyloxypropyltrimethylation.

From the foregoing it is seen that there are a variety of methods for preparing cyclopropyl compounds in the literature. However, the processes in the cited articles are not general in that they do not provide a variety of cyclopropyl compounds in high yields.

It is an object of this invention to provide a method for the preparation of cyclopropane compounds having functional substituents. It is a further object herein to provide cyclopropyl compounds having biological activity, especially pesticidal activity, and functionally substituted cyclopropane compounds having utility as intermediates in the preparation of biologically active materials. It is a further object herein to provide a method for synthesizing cyclopropane carboxylic acids such as chrysanthemic acid. These and other objects are obtained herein as will be seen from the following disclosure.

SUMMARY OF THE INVENTION

The present invention encompasses a process for preparing substituted cyclopropyl compounds of the formula

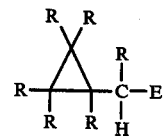

wherein each R is a member selected from the group consisting of hydrogen, alkyl, aryl, alkenyl and substituted alkyl, aryl, and alkenyl substituents, and E is a substituent derived from an electrophile source, comprising admixing an organotin compound of the formula $(CHR=CRCR_2CR_2)_x—SnR^1_{4-x}$ wherein $x$ is an integer of from 1 to 4 and $R^1$ is a member selected from the group consisting of alkyl and substituted alkyl substituents, especially those having 1 to about 20 carbon atoms, with an electrophile source.

The present invention thus encompasses a process for preparing chrysanthemic acid esters comprising:

(1) admixing an organotin compound of the formula

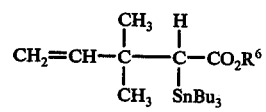

wherein $R^6$ is lower ($C_1$ to $C_5$) alkyl, with an electrophile source of the formula $CH_3C(O)BF_4$;

(2) admixing the product from step (1) with a methylmetallic compound selected from the group consisting of methyl Grignard reagents, methylzinc halides, dimethyl magnesium and methyl alkali metal compounds; and (3) dehydrating the product from step (2).

The present invention further encompasses a process for preparing p-(α-cyclopropyl)-tolyl acetic acids and their derivatives.

In addition, the present invention encompasses various pesticidal cyclopropyl compounds of the type hereinafter disclosed as well as pesticidal methods comprising applying said cyclopropyl compounds to a variety of insect plant, fungi and bacterial pests and/or pest habitats in an amount sufficient to effect the control of said pests.

DETAILED DESCRIPTION OF THE INVENTION

The process of the present invention comprises admixing an organotin compound of the type $(CHR = CRCR_2CR_2)_xSnR_{4-x}^1$ wherein $x$ is an integer of from 1 to 4, R is a member selected from the group consisting of hydrogen, alkyl, substituted alkyl, aryl, substituted aryl, alkenyl and substituted alkenyl substituents and where $R^1$ is a member selected from the group consisting of alkyl and substituted alkyl substitutes with an electrophile source. The reaction proceeds according to the following equation:

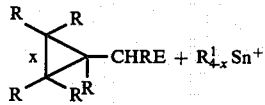

As illustrated by the foregoing equation, the cyclopropylation-demetalation reaction herein is a general one and appears to be independent of the nature of the groups R and alkyl groups $R^1$ in the 3-buentyltin compounds used in the reaction or on the electrophile source. The reaction is carried out by admixing the 3-butenyltin compound with the electrophile source at a temperature from about −65° to about 100° C, preferably around 0° C, and allowing the mixture to stand for periods from about 5 minutes to about 72 hours. The tin moiety is generally recovered as the corresponding oxide or halide from the reaction mixture and the substituted cyclopropyl compound is recovered by standard manipulative processes such as chromatography, distillation, crystallization, etc.

As demonstrated by the equation, the relative molar ratio of the 3-butenyltin compound and the electrophile source employed in the reaction is in the ratio of one mole of electrophile source to one mole of butenyl substituent in the organotin compound. Hence, when a tetrakis-3-butenyltin compound is used in the process herein, four moles of electrophile source per mole of said tin compound are preferably employed. In general terms, sufficient electrophile source is employed to satisfy the stoichiometry of the reaction. Of course, more or less of the source can be employed but the yields will vary. Preferably, one mole of electrophile source per mole of 3-butenyl substituent on the organotin compound is used in the reaction herein.

The 3-butenyltin compounds used in the process of this invention can be prepared in well-known fashion by the reaction of a 3-butenyl Grignard reagent with a tin (IV) halide. Tin tetrahalides, i.e., tin tetrachloride, tin tetrabromide and tetraiodide can be used to prepare tetrakis(3-butenyl)tin compounds of the type used in the present invention. When there are four halogen substituents on the tin, the mole ratio of 3-butenyl Grignard reagent to tin compound is 4:1.

Organotin compounds of the type $R^1_xSnX_{4-x}$, wherein $x$ is an integer of from 1 to 3, wherein X is a halogen, and wherein $R^1$ is an organic substituent as defined above are also useful in preparing 3-butenyltin compounds of the type used in the present process. Included among such organotin compounds are the triorganotin halides, diorganotin dihalides and monoorganotin trihalides. In each instance, the organotin halide is reacted with the 3-butenyl Grignard reagent at a ratio of halogen atoms:Grignard reagent of 1:1.

Exemplary organotin halides useful in preparing the 3-butenyltin compounds used herein are trimethyltin chloride, triethyltin bromide, tripropyltin fluoride, tributyltin chloride, tridecyltin fluoride, tris-dodecyltin fluoride, tris-eicosyltin chloride, dimethyltin dichloride, dimethyltin dibromide, diethyltin difluoride, diethyltin diiodide, dibutyltin dichloride, dibutyltin dibromide, didecyltin dichloride, bis-dodecyltin dichloride, bis-eicosyltin dichloride, methyltin trichloride, ethyltin tribromide, propyltin trifluoride, butyltin trifluoride, butyltin triiodide, decyltin trichloride, eicosyltin trichloride, and the like.

From a cost standpoint, the organotin compounds employed herein to prepare the 3-butenyl organotins are preferably those wherein the halogen is chlorine. Furthermore, the cyclopropylation-demetalation reaction herein appears to be a general one and occurs irrespective of the group $R^1$ on the tin compound. Inasmuch as the tin substituent is not a portion of the cyclopropyl reaction products herein, it is preferable from an economic standpoint to use the simplest organotin compounds available. For this reason, tributyltin chloride, which is commercially available, is the preferred organotin compound used herein; accordingly, 3-butenyltributyltin is preferred for use in the cyclopropylcarbinylation reaction of this invention. From an efficiency standpoint, the tetrakis-(3-butenyl)tin is most efficient in that one mole of this compound will react with four moles of the electrophile source to yield four moles of the substituted cyclopropylcarbinyl compound with the tin being recovered as tin oxide or tin tetrahalide.

The second reactant in the process of this invention is the electrophile source. Electrophile sources useful herein are those electron-seeking agents capable of reacting with the pi-electrons of an olefinic double bond. A variety of such electrophile sources are well-known in the art, including inorganic compounds such as $Cl_2$, $Br_2$, $I_2$, $HgCl_2$, $ZnCl_2$, $AlCl_3$, NOCl, and $SO_3$ and the protonic acids, especially strong mineral acids such as HCl.

Various organic compounds are also known to be electrophile sources. For example, m-chloroperbenzoic acid and m-chloroperbenzoic acid in combination with methyl fluorosulfonate are suitable for use as the electrophile source herein. Another class of electrophile sources suitable for reaction with 3-butenyltin compounds to provide substituted cyclopropyl compounds are the organosulphur compounds having the general formula $R^2SX$, wherein $R^2$ is an alkyl, aryl, substituted alkyl or substituted aryl substituent and X is a halogen. These compounds can be prepared by processes well known in the art. Alkyl groups in such organosulphur halides can range from $C_1$ to $C_{30}$; aryl groups include phenyl, and naphthyl, for example; substituted aryl groups include chlorophenyl, chloronaphthyl, tolyl, xylyl, nitrophenyl, nitronaphthyl, dinitrophenyl, chloronitronaphthyl, chloronitrophenyl, and the like; substituted alkyl groups include hydroxyalkyl, thioalkyl, chloroalkyl, bromoalkyl and the like. Preferred organosulphur electrophile sources herein include 2,4-$(NO_2)_2C_6H_3SCl$ and $2-NO_2-4-ClC_6H_3SCl$.

Another group of electrophile sources herein include what may be termed organic-inorganic adducts of the type $R^3C(O)BF_4$, wherein $R^3$ is an alkyl, aryl, substituted alkyl or substituted aryl substituent, and adducts of the type $R_2^4N^+[ClAg^-]$, wherein $R^4$ is an alkyl, aryl, substituted alkyl or substituted aryl substituent. Such adduct compounds can be prepared by procedures fully set forth in the chemical literature. In the foregoing types of adduct compounds, the substituent groups $R^3$ and $R^4$ can each be alkyl of from $C_1$ to $C_{30}$; aryl groups such as phenyl, naphthyl, tolyl, xylyl, etc.; substituted alkyl such as hydroxyalkyl, thioalkyl, alkoxyalkyl and the like; and the substituted aryl substituents can be, for example, m-nitrophenyl, p-nitrophenyl, dinitrophenyl, β-nitronaphthyl, α-hydroxynaphthyl and alkoxyphenyl such as methoxyphenyl, ethoxyphenyl and the like.

Another class of electrophile sources herein are the organometallic compounds of the formula $R^5MX$, wherein $R^5$ is an alkyl, aryl, substituted alkyl or substituted aryl substituent, M is a metal selected from the group consisting of zinc and mercury, and X is a halogen, e.g., fluorine, chlorine, bromine and iodine. Such organometallic compounds can be prepared, for example, by the reaction of an alkyl halide and the corresponding metal in the manner well known in the art. Representative organometallic electrophile sources herein include those wherein the substituent group $R^5$ is a $C_1$ to $C_{30}$ alkyl group; aryl groups such as phenyl, naphthyl and the like; substituted alkyl groups such as fluoroalkyl, bromoalkyl, nitroalkyl, alkoxyalkyl and the like; and the substituted aryl groups include, for example, fluorophenyl, nitrophenyl, fluoronaphthyl, nitronaphthyl, dinitrophenyl, dinitronaphthyl, chloronitrophenyl, chloronitronaphthyl and the like.

It is to be understood from the foregoing that the cyclopropylcarbinylation reaction of the instant invention appears to be a general one inasmuch as it occurs with substantially all manner of electrophile sources. It is to be further understood that the nature of the organic substituent groups and the substituted organic substituent groups on the said electrophile sources do not appear to have any substantial effect on the cource of the reaction but only provide organic groups having a variety of substituents as group E in the substituted cyclopropylcarbinyl reaction product.

As noted hereinabove, the process of the invention is carried out by simply admixing the 3-butenyltin compound and the electrophile source and allowing them to stand until the reaction is complete. While the reaction can be carried out in the absence of a solvent, it is preferably done using a solvent or liquid suspending medium. For this purpose organic solvents such as diethyl ether, acetic acid and methylene chloride are preferred. However, for convenience, a wide variety of organic solvents can be used including liquid alcohols such as methanol, ethanol and the like; other liquid organic acids such as propanoic acid and butanoic acid; other chlorinated hydrocarbons such as chloroform, carbon tetrachloride, butyl chloride and the like; and liquid organic compounds such as dimethyl formamide and acetonitrile.

The 3-butenyltin compounds used in the practice of the invention can be prepared by well known methods; however, the following specific preparation is presented for illustration purposes.

PREPARATION OF 3-BUTENYLTRIBUTYLTIN

In a 2-liter round bottom flask are placed one liter of diethyl ether, 1.1 moles of magnesium turnings, a small crystal of iodine, and 2 mls. of 3-butenyl chloride. The mixture is heated briefly until the iodine color fades. The mixture is cooled to room temperature and blanketed with nitrogen gas introduced through a side-tube. 3-Butenyl chloride is added dropwise to a total of about 1 mole (∼ 92 mls.) from a constant-pressure dropping funnel to the mixture at a rate of about 1 ml. per 5 minutes. The reaction mixture is heated to reflux during the first 10 minutes of addition to initiate the reaction; following this, the constant addition of the 3-butenyl chloride at the aforementioned rate serves to make the reaction spontaneous. Following addition of all the 3-butenyl chloride, the reaction is allowed to subside, and the reaction mixture is heated to reflux for about 15 minutes to ensure completion. The product, which is the 3-butenyl Grignard reagent, is not isolated but is reacted with tributyltin chloride in situ, as follows.

0.9 Moles of tributyltin chloride are added to the dropping funnel affixed to the reaction flask and added dropwise, with cooling (ice bath) at a rate of about 5 ml. per ten minutes, with constant stirring. Following addition of all the tributyltin chloride, the reaction mixture is refluxed for two hours to insure completion. Following this, the mixture is hydrolyzed to destroy excess Grignard reagent by adding 200 ml. of 0.5M aqueous ammonium chloride solution. Dilute hydrochloric acid is then added slowly to dissolve magnesium hydroxide formed during hydrolysis.

The layers which form on addition of the acid are separated and the ether layer is filtered to remove particulate inorganic matter. The ether layer is dried over sodium sulfate, filtered, and the ether removed on a rotary evaporator. The resulting liquid product is 3-butenyltributyltin.

In the above procedure, the tributyltin chloride is replaced by an equivalent amount of tributyltin bromide, tributyltin iodide, trimethyltin chloride, tridecyltin chloride, and tris-dodecyltin chloride, respectively, and the corresponding 3-butenyl triorganotin compounds are secured.

In the above procedure, the tributyltin chloride is replaced by 0.45 moles of dibutyltin dichloride and bis-(3-butenyl)dibutyltin is secured.

In the above procedure, the tributyltin chloride is replaced by 0.30 moles of butyltrichlorotin and tris-(3-butenyl)butyltin is secured.

In the above procedure, the tributyltin chloride is replaced by 0.22 moles of tin (IV) tetrachloride and tetrakis-(3-butentyl)tin is secured.

The following examples are illustrative of the various aspects of the present invention and are not intended to be limiting thereof.

EXAMPLE I

Preparation of Cyclopropylcarbinyl Bromide

In a 100 ml. 3-necked flask under argon atmosphere were admixed 6.9 g. of 3-butenyltributyltin and 25 ml. of methylene chloride (solvent). 1 ml. of bromine (electrophile source) was added to the solution of the 3-butenyltin compound in dropwise fashion. The reaction was exothermic. The reaction mixture was cooled slightly with a cold water bath until completion. The reaction mixture was transferred to a 100 ml. flask and concentrated on a rotary evaporator with gentle warming. The mixture was distilled at atmospheric pressure to yield a fraction boiling at about 103°–108° C. This fraction was shown by proton nmr to be cyclopropylcarbinyl bromide. Yields were on the order of 80%.

EXAMPLE II

Preparation of Cyclopropylcarbinyl Chloride 6.9 g. of 3-butenyltributyltin was dissolved in 20 ml. of dry $CH_2Cl_2$ in a 50 ml. flask under an argon atmosphere. The flask was equipped with a rubber injection septum and a dry ice-acetone slush condenser. The reaction vessel was immersed in a cooling bath filled with a dry ice-acetone slush (−70° C). The chlorine gas was slowly bubbled through the solution. The reaction was checked for disappearance of 3-butenyltributyltin by gas chromatography. Once g.l.c. analysis indicated that all 3-butenyltributyltin had disappeared, the reaction mixture was transferred to a flask and distilled at atmospheric pressure. The final portion was removed with aspirator vacuum and slight heating. The first cut of the distillate was analyzed by proton nmr and proved to be cyclopropylcarbinyl chloride.

In the above procedure, the 3-butenyltributyltin is replaced by an equivalent amount of 3-butenyltriethyltin and 3-butenyltripentyltin, respectively, and equivalent results are secured. In the above procedure, the 3-butenyltributyltin is replaced by an equivalent amount of tetrakis-(3-butenyl)tin and chlorine gas is introduced into the reaction mixture for a period of time approximately 4-fold that when 3-butenyltributyltin is employed in the process and cyclopropylcarbinyl chloride is secured.

In the above procedure, the chlorine is replaced by an equivalent amount of iodine and cyclopropylcarbinyl iodide is secured.

EXAMPLE III

Preparation of Cyclopropylcarbinyl Alcohol 9.0 g. of the epoxide of 3-butenyltributyltin is prepared from 0.035 moles of 3-butenyltributyltin by warming with 0.035 moles of m-chloroperbenzoic acid.

9.0 g. of the epoxide of 3-butenyltributyltin was dissolved in 10 ml. of dry methylene chloride in a 50 ml. flask under an argon atmosphere. The solution was cooled to 0° C in an ice water bath and HCl gas was bubbled through the solution at a rate of about 0.001 moles/min. After about 0.035 moles of HCl gas had been added, the reaction product was analyzed by gas chromatography and proton nmr. The product proved to be cyclopropylcarbinyl alcohol.

In a variation of the foregoing procedure, the 3-butenyltributyltin and m-chloroperbenzoic acid are admixed in a 1:1 mole ratio in dry methylene chloride and the reaction mixture is refluxed for a period of about 2 hours. The reaction mixture is chromatographed on silica gel and provides a mid-cut which proves to be cyclopropylcarbinyl alcohol.

EXAMPLE IV

Preparation of Cyclopropylcarbinylmercuric Chloride

A mixture comprising 0.69 g. of 3-butentyltributyltin and 25 ml. of $CH_3CN$ was heated to 55° C. A solution comprising 0.54 g. of mercuric chloride in 25 ml. of $CH_3CN$ was added to the suspension of the 3-butenyl-tributyl tin over a 10 minute period. The reaction mixture was stirred for one hour and the solvent was removed on the rotary evaporator. The residue was dissolved in chloroform, cooled and 50 ml. of pentane added thereto. The resulting solution was cooled in a dry ice-acetone bath and filtered to yield 0.52 g. of shining white crystals which proved to be cyclopropylcarbinylmercuric chloride.

In the foregoing procedure, the mercuric chloride is replaced by an equivalent amount of mercuric bromide and mercuric iodide, respectively, and the compounds cyclopropylcarbinylmercuric bromide and cyclopropylcarbinylmercuric iodide are secured.

In the foregoing procedure, the mercuric chloride is replaced by an equivalent amount of zinc chloride, zinc bromide and zinc iodide, respectively, and the compounds cyclopropylcarbinylzinc chloride, cyclopropylcarbinylzinc bromide, and cyclopropylcarbinylzinc iodide are secured.

In the foregoing procedure, the mercuric chloride is replaced by an equivalent amount of aluminum trichloride, aluminum tribromide, and aluminum triiodide, respectively, and the compounds cyclopropylcarbinylaluminum dichloride, cyclopropylcarbinylaluminum dibromide and cyclopropylcarbinylaluminum diiodide, respectively, are secured.

EXAMPLE V

Preparation of Cyclopropylcarbinyl 2-Nitro-4-Chlorophenyl Sulfide

To 1.37 g. of 3-butenyltributyltin was added 0.89 g. of 4-chloro-2-nitrobenzene sulfenyl chloride dissolved in 20 ml. glacial acetic acid at steam bath temperature. The mixture was then heated on a steam bath for 30 minutes and poured into an ice water bath. The product was taken up in diethyl ether, washed twice with 50 ml. portions of water, twice with 50 ml. portions of saturated sodium bicarbonate and an additional time with 50 ml. of water. The resulting ether layer was separated, dried over magnesium sulfate and filtered. The solvent was removed on a rotary evaporator and the concentrate analyzed by proton nmr. The product proved to be cyclopropylcarbinyl 2-nitro-4-chlorophenyl sulfide.

EXAMPLE VI

Preparation of Cyclopropylcarbinyl 2,4-Dinitrophenyl Sulfide

To 1.38 g. of 3-butenyltributyltin was added 0.936 g. of 2,4-dinitrobenzene sulfenyl chloride in 20 ml. glacial acetic acid at steam bath temperature. The reaction mixture was warned on the steam bath for 20 minutes, poured into ice water and filtered. The mixture was extracted with pentane, dried and recrystallized from ethanol to yield cyclopropylcarbinyl 2,4-dinitrophenyl sulfide; m.p. 80°–81° C. Analysis for C and H confirmed the composition of the reaction product.

EXAMPLE VII

Preparation of Cyclopropylcarbinylsulfonate Esters

To 6.88 g. of 3-butenyltributyltin and 200 ml. $CH_2Cl_2$ at −80° C was added 1.77 g. $SO_3$. The reaction mixture was allowed to warm to room temperature and the solvent was removed on a rotary evaporator. Analysis indicated that the product at this time was tributyltin cyclopropylcarbinylsulfonate. 0.5 g. of water was added and the product was allowed to stand for one half hour. 50 ml. of acetone was added and the mixture was stirred.

An etheral solution of diazomethane was added to the foregoing solution until no more bubbles were noted. The solvent was removed on a rotary evaporator and the residue was dissolved in diethyl ether and dried over calcium chloride. Solvent was removed on a rotary evaporator and the residue was distilled (b.p. 68°–72° C at 0.2 mm.). The product, which was recovered in 84% yield, was methyl cyclopropylcarbinyl sulfonate.

In the foregoing procedure, the diazomethane step is deleted and the tributyltin cyclopropylcarbinylsulfonate is recovered by evaporation of the $CH_2Cl_2$ solvent.

In the above procedure, the 3-butenyltributyltin is replaced by an equivalent amount of 2-decyl-3-butenyltributyltin and the resulting product after reaction with diazomethane is methyl 2-decylcyclopropylcarbinylsulfonate. The foregoing ester is hydrolyzed with one molar sodium hydroxide to yield sodium 2-decylcyclopropylcarbinylsulfonate. This latter material, when dissolved in water, exhibits substantial surfactant properties.

EXAMPLE VIII

Preparation of Cyclo-$C_3H_5CH_2NO$ 0.1 Mole of 3-butenyltributyltin is admixed with 0.1 mole of NOCl in $CH_3CN$ at 0° C. The reaction mixture is held at 0° C for 72 hours. The solvent is removed under vacuum and the residue is cyclo-$C_3H_5CH_2NO$.

In the above procedure the 3-butenyltributyltin is replaced by an equivalent amount of 2-chloromethyl-3-butenyltributyl tin and 3-chloromethyl-cyclo-$C_3H_5CH_2NO$ is secured.

EXAMPLE IX

Preparation of Cyclopropylcarbinyl Phenyl Mercury 0.2 Mole of phenylmercuric chloride (commercial) is admixed with a methylene chloride solution of 0.1 mole of bis-(3-butenyl)dibutyltin at −65° C. The reaction mixture is maintained at this temperature for 24 hours, then the solvent is removed by distillation. The residue is chromatographed on silica gel and yields a mid-cut which proves to be cyclopropylcarbinyl phenyl mercury.

In the above procedure the phenylmercuric chloride is replaced by an equivalent amount of p-nitrophenylmercuric chloride, p-chlorophenylmercuric chloride, n-butylmercuric chloride, 3-chlorobutylmercuric chloride, phenylzinc chloride, p-methoxyphenylzinc chloride, m-bromophenylzinc bromide, and n-decylzinc iodide, respectively, and the compounds cyclopropylcarbinyl p-nitrophenyl mercury, cyclopropylcarbinyl p-chlorophenyl mercury, cyclopropylcarbinyl n-butyl mercury, cyclopropylcarbinyl 3-chlorobutyl mercury, cyclopropylcarbinyl phenyl zinc, cyclopropylcarbinyl p-methoxyphenyl zinc, cyclopropylcarbinyl m-bromophenyl zinc, and cyclopropylcarbinyl n-decyl zinc are secured. These compounds exhibit substantial fungicidal activity at solution concentrations of 100 ppm.

EXAMPLE X

Preparation of Cyclopropylcarbinyldimethylamine 0.1 Mole of dimethylchloramine is prepared in standard fashion by admixing 0.1 mole of $(CH_3)_2NH$ with 0.1 mole of NaOCl (as 5.8% aqueous solution of NaOCl) at room temperature.

The dimethylchloramine prepared in the foregoing manner is admixed with 0.1 mole of 3-butenylbributyltin in $CH_2Cl_2$ solvent (500 ml.; 25° C). A solution of 0.1 mole of $AgNO_3$ dissolved in 1 l. anhydrous ethanol is added, portionwise, over 25 minutes and the mixture allowed to stir overnight at room temperature.

The reaction mixture is filtered to remove silver salts and the solvent removed by distillation. The residue is distilled under vacuum to give cyclopropylcarbinyldimethylamine.

In the foregoing procedure the dimethylamine is replaced by an equivalent amount of diphenylamine, di(p-nitrophenyl)amine and diethylamine, respectively and the corresponding disubstituted amino cyclopropylcarbinyl compounds are secured.

The process of the present invention is particularly suitable for preparing chrysanthemic acid esters and chrysanthemic acid-like cyclopropanecarboxylic acid esters. The overall process is illustrated by the following reaction scheme:

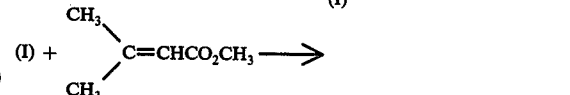

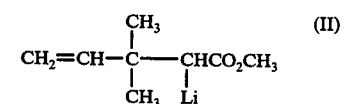

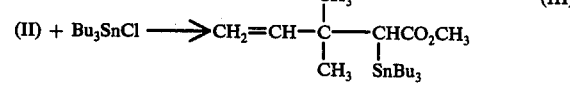

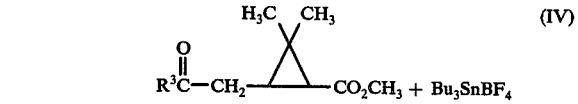

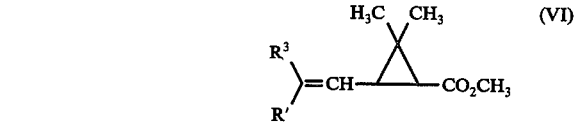

wherein $R^3$ is as defined above and R' is $C_1$ to $C_{10}$ alkyl, substituted alkyl, and aryl, (e.g., phenyl, naphthyl) and substituted aryl. When R and R' are each methyl, the product VI is a chrysanthemate.

EXAMPLE XII

Preparation of Methyl Chrysanthemate

Two moles of vinyllithium (commercial) are admixed with one mole of cuprous iodide in 1 liter of tetrahydrofuran solvent and maintained at reflux for one hour to yield a solution of $(CH_2=CH)_2CuLi$; compound (I) in the foregoing reaction scheme. The solution of compound (I) is admixed with 1 mole of (CH₃)C=CHCO₂CH₃ at 0° C in a Michael-type reaction to yield CH₂=CH—C(CH₃)₂C(Li)HCH₂CH₃; compound (II). Compound (II) is not isolated. The reaction mixture containing (II) is admixed with one mole of tributyltin chloride, portionwise at 0° C and yields methyl 3,3-dimethyl-2-tributylstannyl-4-pentenoate; compound (III). Compound (III) is isolated from the reaction solvent by silica gel chromatography.

0.1 Mole of 3,3-dimethyl-2-tributylstannyl-4-pentenoate (III) prepared in the foregoing manner is dissolved in 500 ml. of acetonitrile. 0.1 Mole of CH₃C(O)Cl is admixed with 0.1 mole of AgBF₄ in 50 ml. of acetonitrile and maintained at room temperature for 10 minutes; this admixing provides AgCl and CH₃C(O)BF₄. The solution of CH₃C(O)BF₄ is added, portionwise, to the solution of compound (III) and the mixture refluxed for one hour. The reaction product is a solution of compound (IV) in the above reaction scheme.

500 mls. of a 2M ether solution of CH₃MgBr (commercial) are added dropwise to the solution of (IV), prepared above, and the mixture is refluxed for 2 hours. After hydrolysis, the solution of compound (V) is eluted through a silica gel column to yield a compound corresponding to (V) in the above scheme.

0.1 Mole of compound (V) prepared in the foregoing manner is admixed with a crystal of iodine in benzene and the mixture is distilled with removal of water. The benzene solution is chromatographed to yield methyl chrysanthemate; compound (VI) in the above scheme.

In the above procedure the methyl Grignard reagent is replaced by an equivalent amount of methyl lithium, methyl sodium, methyl zinc chloride, and dimethyl magnesium, respectively, and methyl chrysanthemate is secured in each instance.

In the above procedure the methyl Grignard reagent is replaced by an equivalent amount of phenyl Grignard, decyl Grignard, p-tolyl Grignard and 3-methoxybutyl Grignard, respectively, and the cyclopropanecarboxylic acid ester of formula VI wherein R' is phenyl, decyl, p-tolyl and 3-methoxybutyl are secured, respectively.

Analogs of chrysanthemic acid are prepared by means of the foregoing process as follows.

0.1 Mole of C₇H₁₅C(O)Cl, 1-NO₂—C₃H₆C(O)Br, 2-CH₃—C₅H₁₀C(O)F and 2-CH₃O—C₁₅H₃₀C(O)I, respectively, are used in the foregoing procedure to replace the CH₃C(O)Cl. The fluoroborates C₇H₁₅C(O)BF₄, 1-NO₂—C₃H₆C(O)BF₄, 2-CH—C₅H₁₀C(O)BF₄ and 2-CH₃O—C₁₅H₃₀C(O)BF₄ are secured, respectively. The foregoing substituted alkyl fluoroborates are respectively admixed (1:1 mole ratio) with compound (III), above, and yield the corresponding substituted analogs of compound (IV), above. The respective substituted cyclopropylcarbinyl compounds are reacted with CH₃MgBr to yield chrysanthemic acid-like esters having groups R' as methyl and R³ groups as C₇H₁₅—, 1-NO₂—C₃H₆—, 2-CH₃—C₅H₁₀— and 2-CH₃O—C₁₅H₃₀—, respectively.

From the foregoing examples it is seen that the cyclopropylcarbinylation reaction herein occurs with all manner of electrophile sources and is not dependent on the type of alkyl or aryl substituent groups in said sources. In addition to the substituents detailed in the foregoing examples, there may also be mentioned the following substituent groups which can be present in the various electrophile sources in the examples; p-bromophenyl, m-ethoxyphenyl, p-trichloromethylphenyl, neopentyl, m-fluorophenyl, naphthyl, β-aminonaphthyl, m-xylyl, m-hydroxyphenyl, benzyl, p-chlorobenzyl, trichloromethyl, pentachloroethyl, and p-thiomethylphenyl.

Also, as can be seen from the foregoing examples, the process of this invention can be carried out with 3-butenyltin compounds containing all manner of substituent groups, R, in the 3-butenyl portion of the tin compound. In addition to the substituted 3-butenyltin compounds detailed in the foregoing examples, 3-butenyltin compounds containing the following substituted 3-butenyl moieties can be employed in the present process; the list is not intended to be limiting inasmuch as the reaction herein is a general one: C(CH₃)₂:C(CH₃)C(CH₃)₂C(CH₃)₂—; C(C₂H₅)₂:C(C₆H₅)CH₂CH₂—; CH₂:CHC(C₆H₅)₂CH₂—; C(p-NO₂C₆H₅)H:CHCH₂CH₂—; C(CCl₃)₂:C(CH₃)CH₂CH₂—; CH₂:CHCH₂C(CHCl₂)H—; CH₂:CHCH₂C(CH₂OH)H—; CH₂:CHC(isobutenyl)₂CH₂—; and CH₂:CHCH₂C(1-chloro-but-2-en)₂—. In each instance, the respective cyclopropylcarbinyl compound containing the various R groups as substituents on the indicated carbon atoms of the cyclopropane moiety are secured when said substituted 3-butenyltin compounds are reacted with an electrophile source in the manner of this invention.

Certain of the novel compounds of this invention are useful for both pre-emergence and post-emergence control of the growth of undesirable vegetation. As employed herein, the term "undesirable vegetation" refers to any unwanted vegetation including seeds, seedlings and germinated plants. Accordingly, a method aspect of the present invention comprises controlling (i.e., preventing, combating, suppressing inhibiting or eradicating) the growth of weeds and other undesirable vegetation by a method which comprises applying to the area or locus infested with such vegetation a growth-controlling amount of a cyclopropylcarbinyl compound of the formula

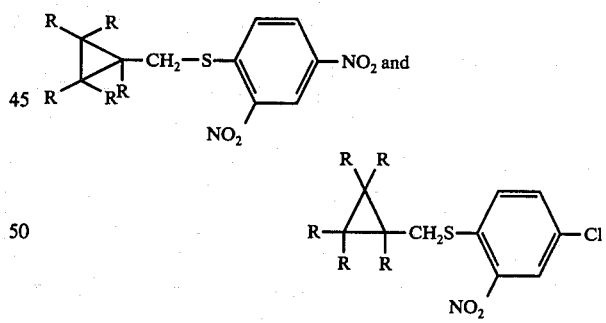

wherein R is as defined above. Preferred herein are compounds wherein each group R is hydrogen. Thus, one aspect of the present invention involves applying to weeds or to earth containing weed seeds a growth-controlling amount of a herbicidal compound of the invention. The growth of a large number of monocotyledonous and dicotyledonous weeds can be inhibited by means of the foregoing compounds. Surprisingly, the compound cyclopropylcarbinyl 2-nitro-4-chlorophenyl sulfide does not inhibit the growth of corn and can be used as a selective herbicide for removing undesirable plant growth from corn fields. The degradability of the compounds of the invention permits substantial control of undesirable vegetation without adverse lingering effect on desirable crops which may be seeded or planted in an area previously treated with a herbicidal compound of the invention.

In accordance with the present invention, undesirable vegetation including weed seeds, seedlings and mature plants, are contacted with the foregoing cyclopropylcarbinyl aryl sulfide compounds in amounts sufficient to achieve the desired degree of control. The required dosage depends upon many factors such as method of application, pre- or post-emergent treatment, type and quantity of vegetation, the particular cyclopropylcarbinyl compounds employed, the nature of the herbicidal formulation, duration of treatment, climatic conditions, etc. Application rates of from 1 to 50, preferably 2 to 10, pounds per acre are normally satisfactory depending on the factors hereinbefore mentioned. The cyclopropylcarbinyl compounds herein can be applied singly or in combination with each other and/or other materials as more fully described hereinafter.

In addition to effecting control of unwanted vegetation, the foregoing cyclopropylcarbinyl aryl sulfide compounds also provide control of insects at the levels used for weed control. These compounds also have acaricidal, bactericidal and fungicidal (i.e., broad range pesticidal) activity. For example, application of cyclopropylcarbinyl 2,4-dinitrophenyl sulfide and cyclopropylcarbinyl 2-nitro-4-chlorophenyl sulfide respectively, to habitats infested with adult house flies, strawberry spider mites, Southern armyworm larvae, Mexican bean beetle larvae, and adult pea aphids kills all of these insect pests. Furthermore, application of the foregoing compounds to test substrates in concentrations of 1000 ppm kills substantially all growing colonies of Candida albicans, Trichophyton mentagrophytes, Glomerella cingulata, Sclerotinia fructicola, Aspergillus niger, Chaetomium globosum, C. botulinum and S. aureus.

In actual usage, the cyclopropylcarbinyl pesticides of this invention are applied to undesirably infested areas in the form of compositions which comprise a carrier and a pest-controlling amount of one or more of the foregoing cyclopropylcarbinyl compounds. Such compositions enable the pesticidal compounds herein to be applied conveniently to the site of the infestation in any desired quantity. These compositions can be solids, such as dusts, granules or wettable powders or the like, or they can be liquids such as solutions, aerosols, emulsifiable concentrates or the like. The solid compositions generally contain from about 1% to about 95% by weight of the cyclopropylcarbinyl compounds while the liquid compositions generally contain from about 0.5% to about 70% by weight of said compounds.

Suspensions or dispersions of the compounds of the invention in a non-solvent, such as water, are suitably employed in treating plant foilage. Also suitably employed are solutions of the pesticides of the invention in oil which is emulsified in water. Examples of oil solvents include hydrocarbons such as benzene and toluene and halogenated hydrocarbons such as chlorobenzene, chloroform, fluorotrichloromethane and dichlorodifluoromethane.

Aerosols prepared by dissolving the foregoing compounds in a highly volatile liquid carrier such as trifluorochloromethane, or by dissolving such compounds in a less volatile solvent, such as benzene, and admixing the resulting solution with a highly volatile liquid aerosol carrier can also be employed to advantage.

Preferred liquid pesticidal compositions for the practice of the invention herein are emulsifiable concentrates which comprise a compound selected from the group consisting of

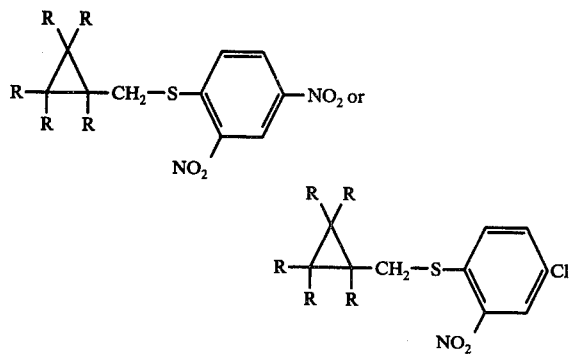

especially those wherein each R is hydrogen, an emulsifier, and a solvent carrier. Such concentrates can be extended with water and/or oil to any desired concentration of the herbicide for application as sprays to the site of vegetative investation. The emulsifiers used in these concentrates are surface active agents of the anionic, nonionic, cationic, ampholytic or zwitterionic type.

Examples of suitable anionic surface active agents are sodium salts of fatty alcohol sulfates having from 8–18 carbon atoms in the fatty chain and sodium salts of alkyl benzene sulfonates having from 9 to 15 carbon atoms in the alkyl chain.

Examples of suitable nonionic surface active agents are the polyethylene oxide condensates of alkyl phenols, wherein the alkyl chain contains from about 6 to 12 carbon atoms and the amount of ethylene oxide condensed onto each mole of alkyl phenol is from about 5 to 25 moles.

Suitable cationic surface active agents include dimethyl dialkyl quaternary ammonium salts wherein the alkyl chains contain from about 8 to 18 carbon atoms.

Suitable ampholytic surface active agents include derivatives of aliphatic secondary or tertiary amines in which one of the aliphatic substituents contains from about 8 to 18 carbon atoms and one contains an anionic water solubilizing group, e.g., sulfate or sulfo. Specific suitable ampholytic surface active agents are sodium 3-dodecylaminopropionate and sodium 3-dodecyl amino propane sulfonate.

Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio) propane-1-sulfonate and 3-(N,N-dimethyl-N-hexadecylammonio)-2-hydroxypropane-1-sulfonate.

Other suitable surface active agents are described in Detergents and Emulsifiers — 1969 Annual by John W. McCutcheon Inc. which is incorporated by reference herein. Suitable solvents for these emulsifiable concentrates include those mentioned hereinbefore.

Suitable dusts can be prepared by admixing the active compounds of the invention with dry free-flowing powders such as clay, bentonite, fuller's earth, diatomaceous earth, pyrophyllite, attapulgite, calcium carbonate, chalk or the like. An amount of active compound of up to about 5% is preferred and is suitable for most applications.

The compounds of the present invention are also useful when combined with other biocides and insecticides, herbicides, and/or defoliants, dessicants and the like in the compositions heretofore mentioned. These other materials can comprise from about 5% to about 95% by weight of the total active ingredients in said compositions.

The following example illustrates a pesticidal composition employing certain of the novel compounds herein but is not intended to be limiting of such compositions.

EXAMPLE XIII

| Ingredient | Percent (wt.) |
|---|---|
| Cyclopropylcarbinyl 2,4-dinitrophenyl sulfide | 10.0 |
| Petroleum Distillate | 25.0 |
| Kyro EOB (emulsifier) | 1.5 |
| Water | Balance |

The above composition is sprayed onto areas infested with thistle, chickweed, dandelions, quackgrass and Jimpson weed at a rate of 35 gallons/acre and these weeds are substantially reduced.

The above composition is applied to areas infested with spider mites, ants, boring beetles, corn borers and aphids at a rate of 25 gallons/acre and substantially all such pests are destroyed.

In the above composition the cyclopropylcarbinyl 2,4-dinitrophenyl sulfide is replaced by cyclopropylcarbinyl 2-nitro-4-chlorophenyl sulfide, 2-methylcyclopropylcarbinyl 2,4-dinitrophenyl sulfide, 2,3-dimethylcyclopropylcarbinyl 2-nitro-4-chlorophenyl sulfide, 2-phenylcyclopropylcarbinyl 2,4-dinitrophenyl sulfide, 1-methyl cyclopropylcarbinyl 2,4-dinitrophenyl sulfide, and 1-phenylcyclopropylcarbinyl 2,4-dichlorophenyl sulfide, respectively, and equivalent results are secured.

Certain of the cyclopropylcarbinyl compounds prepared in the manner of this invention contain metallo substituents and such compounds are useful as pesticides and are especially useful for preventing marine fouling of ships, pilings and other submerged objects. For example, the compounds tributyltin cyclopropylcarbinylsulfonate, cyclopropylcarbinylmercuric chloride, cyclopropylcarbinyl phenyl mercury and cyclopropylcarbinylzinc chloride are especially suited for this anti-fouling use.

The metallo-cyclopropylcarbinyl anti-fouling agents of this invention can be applied to the surface being treated alone, but are preferably applied in combination with various carrier materials, said carriers serving both as diluents and as penetrants for carrying the compounds into the interstices of the treated surface. Preferably, the carriers suitable for use in the present process are inexpensive non-staining materials capable of solubilizing the cyclopropylcarbinyl compounds. Suitable carrier materials herein include, for example, the chlorinated hydrocarbons such as trichloroethylene, chlorobenzene, propylene chloride, alkyl and aromatic hydrocarbons such as benzene, toluene, xylene, hexane, decane, and mixtures thereof such as the petroleum ethers, kerosenes and naphtha fractions. Creosote can also be employed, but the resulting treated surfaces are not paintable. Any of the non-aqueous carriers commonly used for anti-fouling compounds and wood preservatives can also be used herein. Such non-aqueous carriers are commonly "extended" with water prior to use.

Various film-forming carriers such as drying oils commonly employed as paint bases, for example, rapeseed oil, linseed oil, dehydrogenated soybean oil, turpentine fractions and the like as well as commercial film-forming latex and polymer-based paint vehicles are preferred carriers herein. Epoxy resin paint bases are especially preferred carriers of the anti-fouling compounds herein and come within the definition of preferred film forming carriers.

The following example illustrates an anti-fouling composition containing a metallo-cyclopropylcarbinyl compound as the anti-fouling agent.

EXAMPLE XIV

An anti-fouling ship's paint formulation corresponding substantially to MIL-P-22299, as published in "Guide to United States Government Paint Specifications" 16th ed., National Paint, Varnish and Lacquer Association, Washington, D.C., supplement 11, June, 1965, is prepared having the following composition:

| Ingredient | Parts by Weight |
|---|---|
| cyclopropylcarbinylmercuric chloride | 200 |
| rosin | 32 |
| polyisobutylene polymer | 45 |
| xylene | 864 |
| Deenax* | 0.05 |

*Inhibitor

The above composition is brushed onto concrete, steel and aluminum plate at a rate of about 1 gallon per 500 square feet; the coated surfaces are allowed to dry and are then immersed in ocean water. Upon retrieval, the coated surfaces are substantially free from mollusks, barnacles, encursging bryozoans, fungi, algae, begula, hydroids, oysters, tube worms, tunicates, and microorganism slime film.

In the above composition, the cyclopropylcarbinyl mercuric chloride is replaced by an equivalent amount of cyclopropylcarbinylzinc chloride, cyclopropylcarbinyl phenyl mercury and tributyltin cyclopropylcarbinyl sulfonate, respectively, and equivalent results are secured.

The anti-fouling compositions herein comprise from 50% to 99% by weight of a film-forming carrier and from 1% to 50% by weight of a cyclopropylcarbinyl metal compound of the type disclosed above. The compositions can contain other standard paint additives such as pigments, polymerization accelerators, extenders, suspension agents and the like. These do not affect the anti-foulant properties of the compositions.

As can be seen from the foregoing, compounds of the formula

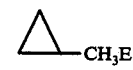

wherein E is a member selected from the group consisting of —HgX, ZnX, where X is a halogen, especially chloride; —SO$_3$SnR$_3^1$, wherein R$^1$ is selected from alkyl and substituted alkyl; and

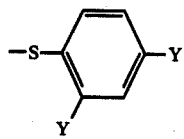

wherein each Y is selected from —NO₂ and —Cl, are useful in the pesticidal and anti-fouling compositions herein.

As mentioned earlier, another class of compounds which can be prepared by the process of the present invention are those having the general formula:

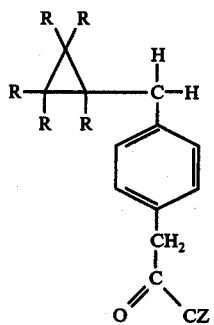

wherein each R is a member selected from the group consisting of hydrogen, alkyl, aryl, alkenyl and substituted alkyl, aryl, and alkenyl substituents and Z is R or a pharmaceutically acceptable salt forming anion such as alkali metals (e.g., sodium and potassium), alkaline earth metals (e.g., stanno and indium) ammonium and low molecular weight substituted ammonium (e.g., mono-, di-, and triethanolamine).

Such compounds and especially those wherein each R is hydrogen are known anti-inflammatory agents which heretofore were difficult to prepare. These compounds can be readily prepared in accordance with the present invention as described in the following Example.

EXAMPLE XV p-(α-cyclopropyl)-tolyl acetic acid is prepared by the following reaction scheme:

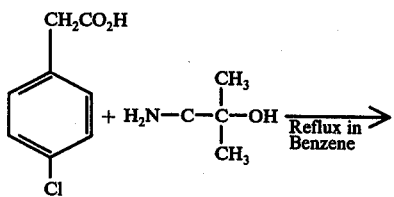

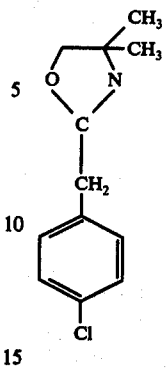

In this step, any of the carboxylic acid protecting groups known in the art can be used in place of 2-amino-iso-butanol as this group is hydrolyzed off in the final step.

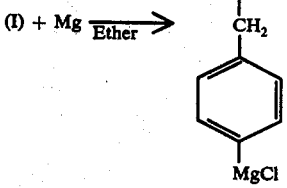

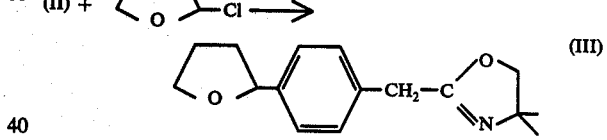

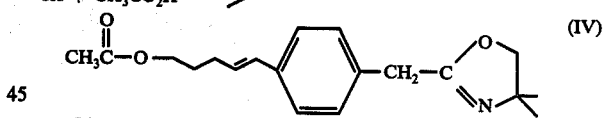

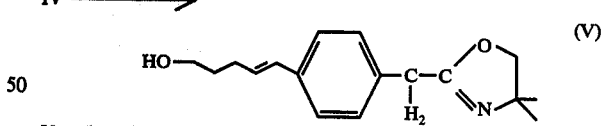

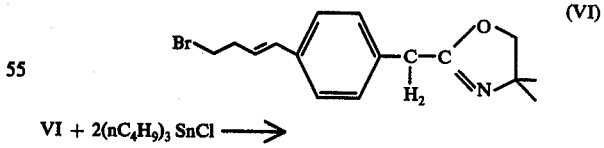

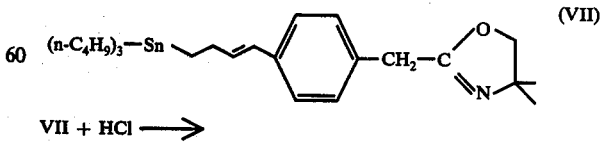

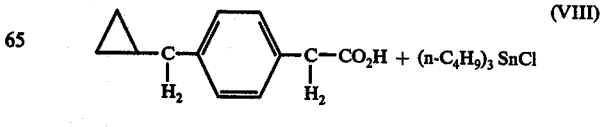

One mole of 4-(p-substituted phenyl)-3-butenyl-1-acetate (IV) in 500 mls of ether are added to 0.5 moles of lithium aluminum hydride dispersed in 200 mls of ether. The mixture is refluxed for 4 hours and then cooled to room temperature. A saturated solution of ammonium chloride is added until the precipitate turns white and the ether layer separates. The white precipitate is washed several times with saturated ammonium chloride and the washings are extracted with ether. The combined ethereal extracts are dried (magnesium sulfate) and concentrated in vacuo with a yield of 4-(p-substituted phenyl)-3-butenyl-1-ol (IV) of about 80%.

To a solution of 0.5 moles of 4-(p-substituted phenyl)-3-buten-1-ol produced above and 0.5 mole triphenylphosphine in 500 mls DMF was added 80 gms of bromine (0.5 mole). During the addition cooling is supplied to keep the reaction temperature below 55°. Addition of bromine is stopped when a persistent orange color is noted. All volatile materials are distilled at 5 mm. into a receiver cooled in a dry ice/acetone bath (−80°). The distillate is diluted with 500 mls of water and the organic phase separated, dried (magnesium sulfate), and distilled to yield 4-bromo-1-(p-substituted phenyl)-1-butene (VI) in about 80% of theoretical yield.

To a Grignard prepared from 0.5 mole 4-bromo-1-(p-substituted phenyl)-1-butene (VI) and 18 gms (0.75 mole) magnesium in 200 mls ether is added 162 gms tributyltinchloride. The reaction is refluxed six hours and then cooled slowly to room temperature. The solids are filtered off and the ether layer washed with water, dried (magnesium sulfate) and concentrated in vacuo yielding 4-(p-substituted phenyl)-3-butenyltributyltin (VII) which is placed in 100 mls of dioxan at 0° C; HCl is added and the mixture is allowed to warm to room temperature and is fractionally distilled to yield p-(α-cyclopropyl)-tolyl acetic acid (VIII).

Having thus described the present invention with reference to several specific embodiments thereof, what is claimed is:

1. A process for preparing cyclopropylcarbinyl alcohol of the formula

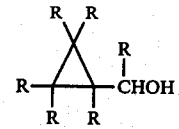

wherein each R is hydrogen, comprising admixing an organotin compound of the formula

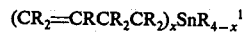

wherein $x$ is an integer of from 1 to 4 and $R^1$ is an alkyl substituent, and R is hydrogen, with m-chloroperbenzoic acid and warming to form the corresponding epoxide and, thereafter reacting said epoxide with hydrogen chloride to produce said cyclopropylcarbinyl alcohol.

2. A process according to claim 1 wherein the organotin compound is a 3-butenyltributyltin.

3. A process according to claim 1 wherein the organotin compound is tetrakis-(3-butenyl)tin.

4. A process according to claim 1 wherein the organotin compound is tetrakis-(3-butenyl)tin and the mole ratio of organotin compound:electrophile source is 1:4.

5. A process according to claim 1 in which the reaction of the organotin compound and m-chloroperbenzoic acid is carried out in the presence of methylene chloride solvent.

* * * * *